United States Patent [19]

Hagemann et al.

[11] 3,951,660

[45] Apr. 20, 1976

[54] DRY COPYING MATERIAL

[75] Inventors: Hermann Hagemann, Cologne; Anita von Konig, Leverkusen, both of Germany

[73] Assignee: AGFA-Gevaert, A.G., Leverkusen, Germany

[22] Filed: Dec. 17, 1974

[21] Appl. No.: 533,672

Related U.S. Application Data

[63] Continuation-in-part of Ser. No. 424,205, Dec. 13, 1973.

[30] Foreign Application Priority Data

Dec. 16, 1972 Germany .......................... 2261739
June 2, 1973 Germany .......................... 2328145

[52] U.S. Cl. .......................... 96/67; 96/48 HD; 96/114.1; 96/114.6; 260/244 R; 260/240.4

[51] Int. Cl.$^2$ .......................... G03C 1/02; C07D 265/00

[58] Field of Search .......................... 96/87 R

[56] References Cited

UNITED STATES PATENTS 3,589,903 6/1971 Birkeland .......................... 96/67

*Primary Examiner*—David Klein
*Assistant Examiner*—Alfonso T. Suro Pico
*Attorney, Agent, or Firm*—Connolly and Hutz

[57] ABSTRACT

A material for use in a process of producing optical copies of graphic originals, which optical recording material is in a layer and contains a nonlight sensitive silver salt, such as silver behenate, and a toner compound in a binder. The layer is suitably supported. The toner compound is of the following formula:

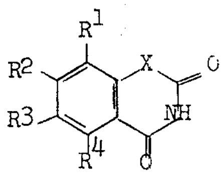

in which

X represents O or $NR^5$;

$R^1$, $R^2$, $R^3$ or $R^4$ represent (1) hydrogen, (2) alkyl, preferably with up to 20 and more, preferably with up to 4 carbon atoms, (3) cycloalkyl, especially cyclopentyl or cyclohexyl, (4) alkoxy, preferably with up to 2 carbon atoms, (5) alkylthio with preferably up to 2 carbon atoms, (6) hydroxy, (7) dialkylamino, the alkyl radicals also containing preferably up to 2 carbon atmos or (8) halogen, preferably chlorine or bromine; in addition to which $R^1$ and $R^2$ or $R^2$ and $R^3$ or $R^3$ and $R^4$ may represent the ring members required to complete a fused aromatic ring, preferably a benzene ring; represents alkyl with preferably up to 20 and more, preferably with up to 2 carbon atoms.

13 Claims, No Drawings

DRY COPYING MATERIAL

This application is a continuation-in-part of U.S. application Ser. No. 424,205, filed Dec. 13, 1973, by Hermann Hagemann and others, entitled "Dry Copying Material", now copending.

The present invention relates to recording materials for producing color tone improved copies of graphic originals in a dry way.

Photographic processes which give dry copies of an original are known per se. The material involved are essentially materials containing light- or heat-sensitive layers. These layers are imagewise exposed or heated to form an image which initiates a coloring reaction resulting in the formation of the image.

In the copying process described in U.S. Pat. No. 3,152,904, recording materials are used which contain an oxidizing agent, a reducing agent and a relatively small quantity of a light-sensitive compound. A colored image is formed by a redox reaction in the exposed and subsequently heated areas. The oxidizing agents used are organic silver salts whilst the reducing agents are aminophenols, hydroxylamines, pyrazolidones or phenols, also phenylenediamine or etherified naphthols, for example 4-methoxy-1-naphthol. Heavy metal salts are suitable for use as light-sensitive compounds, forming traces of the free metal on exposure. The heavy metal salts are in particular light-sensitive silver salts, for example silver halides, which photolytically form silver on exposure to light. The redox reaction is initiated by these photolytically formed heavy metal nuclei.

The above systems are utilized in combination with non-lightsensitive silver salts as oxidizing agents, for example silver saccharide or silver salts of long-chain fatty acids. A particularly high degree of light-sensitivity is obtained when the silver halide required is produced on the surface of the non-lightsensitive silver salt by reaction with halide ions or a compound which forms halide ions, for example by the process described in U.S. Pat. No. 3,457,075. These materials are sensitive in the short-wave region of the spectrum, corresponding to the natural sensitivity of the silver halides used, and can also be sensitized to light of longer wavelength by the addition of spectral sensitizing dyes.

In another known process for the production of dry photographic copies, a photographic material containing a silver salt and a reducing agent for this silver salt is exposed to form an image, and the exposed material is heated to a temperature at which the reducing agent reduces the silver compound at the exposed areas to form a visible silver image. The photographic material for this process includes a layer containing a silver compound which is substantially non-lightsensitive under the conditions of the process, a reducing agent and a polymethine sensitizer for spectrally sensitizing the non-lightsensitive silver compound, is used for this process.

In other known processes for producing copies by exposing a layer, containing a light-sensitive compound and an image-producing compound capable of being heat-transferred into an image-receiving layer, to form an image, the image-producing compound is converted at the exposed areas into a non-transferable compound, the exposed layer brought into contact with an image-receiving layer containing compounds which react with the image-producing compound to form colored compounds, and the layers while in contact heated to a temperature at which the image-producing compound is transferred from the unexposed areas of the light-sensitive layer into the image-receiving layer.

Copying processes of this kind also include the process described in U.S. Pat. No. 3,094,417, in which light-sensitive layers containing a transferable compound and a dye are used. On exposure to light, the transferable compound, for example 4-methoxy-1-naphthol, is converted into a non-transferable product.

U.S. Pat. No. 3,619,237 describe a similar process, in which acetoacetonitrile, pyrazolidin-3-one or pyrazolin-5-one derivatives which can be inactivated by light, are transferable under heat and reactive with a silver salt, are used.

Unless suitable measures are taken, it is only possible in all of these processes to obtain yellow to yellowish brown silver images of poor contrast. Better contrast can be obtained by increasing the quantity of reducing agent in the materials used. Unfortunately, this measure is attended by the following disadvantages. The quantity of the transferable reducing agent present in the light-sensitive material has to be kept to a minimum if the exposure time is intended to be short. The quantity of reducing agent present in the non-lightsensitive image-receiving material must be kept as small as possible to prevent the casting solution for these layers or the layers themselves from undesirably darkening, i.e. to prevent reduction of the organic silver salts during the preparation and storage of the material. Accordingly, it is preferred to add to these materials weak reducing agents of the o-alkyl-substituted phenol type, of the kind described for example in U.S. Pat. No. 3,218,166 for the non-lightsensitive image-receiving materials. The degree of reduction occuring in the image-receiving material during the image formation is accordingly limited.

The quantity of reducing agent present in the light-sensitive silver-salt-containing layers as well has to be kept to a minimum to prevent the casting solution or the layer from undesirably turning dark, i.e. to prevent reduction of the organic silver salts during the preparation and storage of the material. For this reason, it is preferred to add to these materials also weak reducing agents of the o-alkyl-substituted phenol or hydroxycoumarane and hydroxychromane type as described, for example, in British Pat. Specification No. 1,264,532, and Belgian Pat. No. 768,374.

In order to obtain images of adequate optical density which provide an adequate degree of contrast in the finished copy, so-called toners which shift the color of the image towards brown to black can be added to the image-receiving layers. Compounds of this kind are, for example, 2H-phthalazin-1-one, barbituric acid, saccharin and 2-mercapto-benzoxazole, phthalimides and 2-acyl-2H-phthalazin-1-ones. In most cases, the effect of these toners is not sufficient. Some compounds of this kind inhibit development or discolor the whites of the image-receiving material during heating or, in combination with some silver salts and reducing agents, cause the casting solution or the materials to turn dark, thus restricting their utility.

Heat-sensitive copy-sheets capable of undergoing a color change by the thermally initiated reduction of a silver compound with an organic reducing compound are known from British Pat. No. 866,076. Image-forming reactants disclosed in said patent are silver behenate and 2,3-dihydroxybenzoic acid.

A heat-sensitive copy-sheet containing said compounds is suited for the thermographic copying of originals containing infrared-absorbing image markings. When the original is exposed to infrared-radiation in thermoconductive contact with such copy-sheet, the infrared-absorbing image portions of the original are selectively heated and by heat transfer cause the development in the adjacent heat-sensitive sheet of a silver image corresponding with the image markings of the original.

It is among the objects of the invention to provide toner compounds for dry recording processes described above which make the silver image black in color without retarding development and not adversely affecting the stability of the material during production or storage.

Accordingly, the invention relates to recording materials for the production of copies in a dry way with a layer containing essentially non-lightsensitive reducible silver salts, preferably a reducing agent and a heterocyclic toner compound of the formula

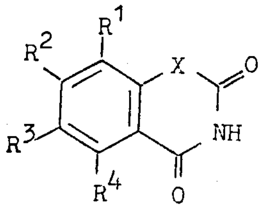

in which

X represents O or $NR^5$;

$R^1$, $R^2$, $R^3$ or $R^4$ represent (1) hydrogen, (2) alkyl, preferably with up to 20 and more, preferably with up to 4 carbon atoms, (3) cycloalkyl, especially cyclopentyl or cyclohexyl, (4) alkoxy, preferably with up to 2 carbon atoms, (5) alkylthio with preferably up to 2 carbon atoms, (6) hydroxy, (7) dialkylamino, the alkyl radicals also containing preferably up to 2 carbon atoms or (8) halogen, preferably chlorine or bromine;

in addition to which $R^1$ and $R^2$ or $R^2$ and $R^3$ or $R^3$ and $R^4$ may represent the ring members required to complete a fused aromatic ring, preferably a benzene ring;

$R^5$ represents alkyl with preferably up to 20 and more, preferably with up to 2 carbon atoms.

The materials of the present invention can be used for the dry recording processes described hereinbefore including the following embodiments:

1. Production of a photographic image by exposing and heating the photographic layer to produce a silver image. In this case the material of the present invention in addition contains a light-sensitive heavy metal compound preferably a light-sensitive silver salt and/or a polymethine sensitizer for spectrally sensitizing the non-light-sensitive silver salts.
2. Production of a photograhic image in an image-receiving layer by exposing a light-sensitive layer containing a transferable reducing agent which is rendered non-transferable at the exposed areas and heating the exposed layer to transfer the reducing agent from the unexposed areas to the image-receiving layer to produce a silver image therein by reduction of the non-lightsensitive silver salt in the said image receiving layer. In processes of this kind, the material of the present invention is utilized as image-receiving layer.
3. Production of thermographic images by imagewise heating the material of the present invention thereby forming a silver image.

Quinazolin dione and benzoxazin or naphthoxazin dione derivatives corresponding to the following formulae are particularly suitable:

1 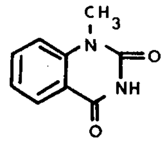 244°C

2 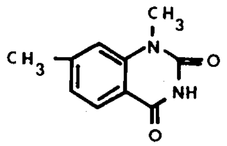 243°C

3 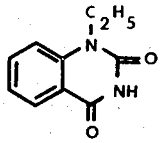 215°C

4 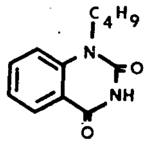 127°C

5 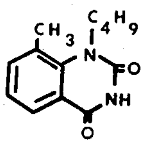 159–163°C

6 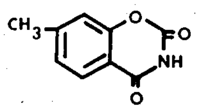 228°C

-continued
| | | |
|---|---|---|
| | 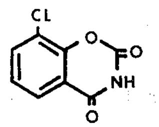 | 238°C |
| | 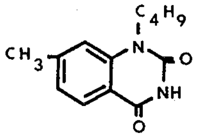 | 162°C |
| | 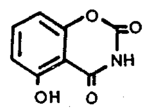 | 203°C |
| | 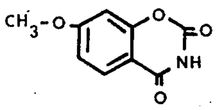 | 216–217°C |
| | 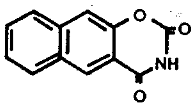 | 240°C |
| | 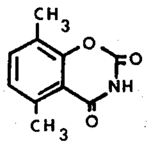 | 238°C |
| | 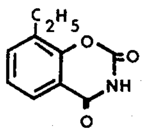 | 150°C |
| | 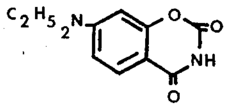 | 219°C |
-continued
| | | |
|---|---|---|
| 15 | 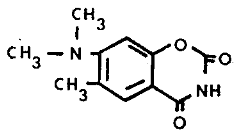 | 236°C |
| 16 | 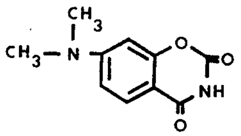 | 299°C |
| 17 | 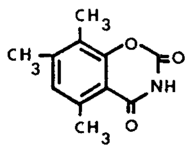 | 257–259°C |
| 18 | 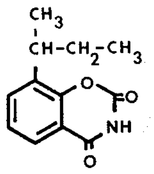 | 168°C |
| 19 | 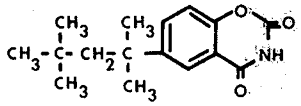 | 168°C |
| 20 | 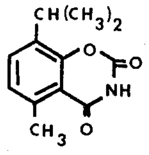 | 152°C |
| 21 | 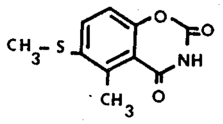 | 260°C |

-continued
| | | |
|---|---|---|
| 22 | 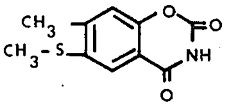 | 254°C |
| 23 | 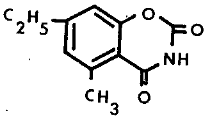 | 155°C |
| 24 | 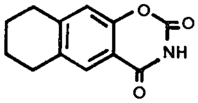 | 236°C |
| 25 | 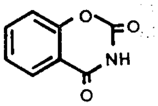 | 226–227°C |
| 26 | 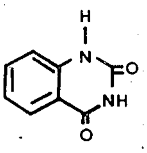 | >300°C |
| 27 | 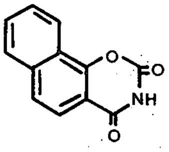 | 280°C |
| 28 | 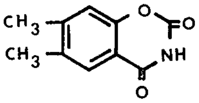 | 255°C |
| 29 | 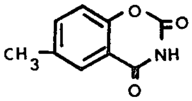 | 237°C |
| 30 | 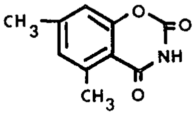 | 223°C |
-continued
| | | |
|---|---|---|
| 31 | 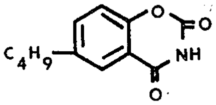 | 164°C |
| 32 | 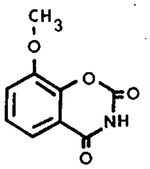 | 255°C |
| 33 | 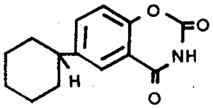 | 204°C |
| 34 | 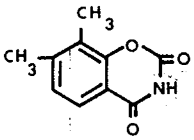 | 226°C |
| 35 | 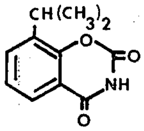 | 179°C |
| 36 | 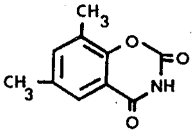 | 219°C |
| 37 | 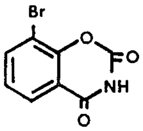 | 243°C |

-continued

| | | |
|---|---|---|
| 38 | 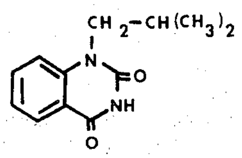 | 161°C |

The aforementioned heterocyclic compounds can be obtained, for example, by reacting phenols or secondary aromatic amines with N-chlorocarbonylisocyanate.

The reaction is preferably carried out with a substantially equimolar quantity of N-chlorocarbonylisocyanate, if desired in the presence of an inert organic solvent, at a temperature of from −100° to +280°C. In general, the reaction is carried out at temperatures of from 0° to +220°C and preferably at temperatures of from +20° to +160°C.

The reaction components are generally used in substantially stoichiometric quantitative ratios. In order to avoid intermolecular secondary reactions and to obtain as complete a conversion as possible, it can be of advantage to use the N-chlorocarbonylisocyanate in an excess of up to 50 % by weight, preferably up to 20 % by weight.

Methylene chloride, chloroform, chlorobenzene and o-dichlorobenzene are examples of inert, organic solvents which are suitable.

It has generally proved to be of advantage initially to introduce the chlorocarbonyl isocyanate and, following addition of the phenol or secondary aromatic amine, to add a Friedel-Crafts catalyst, preferably ferric chloride, in a quantity of from 0.1 to 5 % by weight and preferably in a quantity of from 0.5 to 2 % by weight, based on the total weight of the reaction mixture, and/or to carry out the reaction during heating at least partly in a closed vessel, in which case the hydrogen chloride liberated may take over the function performed by the Friedel-Crafts catalyst.

After cooling of the reaction mixture, the reaction products generally accumulate in highly pure form or, if necessary, are processed in the usual way.

COMPOUND 10

744 g (6 mols) of 3-methoxyphenol in 2 liters of chlorobenzene are added over a period of about 2 hours at 28 to 30°C to a solution of 655 g (6.2 mols) of N-chlorocarbonylisocyanate in 1 liter of chlorobenzene. The reaction mixture is heated until there is no further evolution of hydrogen chloride, after which the deposit is filtered off under suction and washed with petroleum ether. Compound 10 which has a melting point of 216° – 217°C is obtained in a yield of 990 g (86 % of the theoretical).

| Elementary analysis: | | | | |
|---|---|---|---|---|
| calculated: | C 56.0 | H 3.63 | N 7.25 | O 33.2 |
| found: | C 56.0 | H 3.70 | N 7.30 | O 33.2 |

Compound 17

86 g (84 % of the theoretical yield) of compound 17 are obtained from 63 g (0.6 mol) of ClCONCO, dissolved in 400 ml of o-dichlorobenzene, 68 g (0.5 mol) of 2,3,6-trimethylphenol and 3 g of $FeCl_3$ after heating for 5 hours to 170°C and working up in the same way as described for compound 10.

Melting point: 257° – 259°C (from n-propanol)

| Elementary analysis: | | | | |
|---|---|---|---|---|
| calculated: | C 64.3 | H 5.37 | N 6.83 | O 23.4 |
| found: | C 64.5 | H 5.20 | N 6.80 | O 23.5 |

Compound 25

Solutions of 211 g (2 mols) of ClCONCO in 400 ml of chlorobenzene and of 188 g (2 mols) of phenol in 400 ml of chlorobenzene are combined and heated for 3 hours to 220°C in an autoclave, followed by working up in the same way as described for compound 10.

Compound 25 which has a melting point of 226° – 227°C is obtained in a yield of 89 %.

The other compounds in the formula table given above can be similarly prepared.

The photographic materials according to the invention containing a quinazolin dione and naphthoxazin or benzoxazin dione derivative are used in the above-described processes for the production of dry silver images.

By adding the toners according to the invention, the silver images are changed from yellowish-orange to darkbrown-black/blue-black in color in the required manner. The stability of the casting solutions for the layers and the stability of the layers themselves are not adversely affected by the addition of these toners.

In addition, the photographic properties, such as developability, are surprisingly stabilized by comparison, for example with the materials containing phthalazinone toners, especially under adverse storage conditions such as elevated temperature.

The first kind of processes yield directly a silver image upon imagewise exposure and heating of the exposed layer. The photographic material used comprises a layer containing a non-lightsensitive silver salt and generally small quantities of a photosensitive heavy metal salt and if desired a polymethine dye, especially a silver salt, and a reducing agent for reducing the silver salts at the exposed places. Another photographic material which is also suitable for this kind of processes comprises a layer containing a silver compound which is substantially non-lightsensitive under the conditions of the process, a reducing agent and a small quantity of a polymethine sensitizer for spectrally sensitizing the non-lightsensitive silver salt, as described in U.S. Application Ser. No. 279,573.

The sensitizers are generally added to the casting solutions described later in solution in organic solvents. They can also be added in solid form to the silver salt before it is ground or even just before the casting solution is applied to a support. The concentration of the sensitizer in the layer can vary within wide limits. It is governed both by the required effect and by the type of sensitizer in combination with the silver salt. In general, concentrations of from 0.01 to 2.0 g of sensitizing dye, preferably 0.2 to 0.6 g per mol of silver salt, have proved to be sufficient. In individual cases, the sensitizers can also be added in quantities outside this range.

The toners used in accordance with the invention are preferably added to the light-sensitive layer. However, they can also be added either wholly or in part to an adjacent layer.

The second kind of processes are transfer processes for the production of dry positive copies, employing light-sensitive photographic materials with a layer containing a reducing agent transferable at temperatures of from 80 to 200°C and a light-sensitive substance which at the exposed places activates the oxygen (triplet) which converts the reducing agent by oxidation into non-transferable form.

The layer is exposed to the original to be reproduced and then brought into contact with the image-receiving layer of a photographic material containing a non-light-sensitive silver compound and advantageously a weak reducing agent and the toners according to the invention. The layers while still in contact are heated, as a result of which the reducing agent is transferred from the unexposed areas of the light-sensitive layer to the image-receiving layer where it reduces the non-light-sensitive silver salt to form a positive silver image of the original.

The toner compounds used according to the invention can be added to the layers in various quantities. The optimum quantity is governed both by the required effect and by the composition of the layer. The optimum quantity for any given case can readily be determined by a few simple tests known in the art. In general, it has proved to be sufficient to add the toner compounds in quantities of from 0.2 to 6 mols and preferably in quantities of from 0.3 to 5 mols per mol of the non-lightsensitive silver compound, preferably an organic silver salt.

The toner compounds used according to the invention can also be employed in admixture with conventional toners. The concentration of the additional toners is preferably lower than the toners according to the invention. Reference is made to unsubstituted phthalazinone, phthalazinone derivatives, phthalimide or phthalimide derivatives, for example those described in Belgian Patent No. 787,340 and German Offenlegungsschriften No. 21 40 063, 22 20 597 or 22 20 618.

The toners used according to the invention can be used in combination with materials and compounds known for the particular heat-developing process, i.e. for the silver-salt-containing light-sensitive or heat-sensitive copying material or silver-salt-free light-sensitive material and for the heat-sensitive non-lightsensitive image-receiving material, for example reducing agents binders, silver salts and other heavy metal salts, white pigments and stabilizers. Materials of this kind are known per se and are described, for example, in the following U.S. Pats.: Nos. 3,074,809; 3,728,115; 3,107,174; 3,457,075; 3,460,946; 3,589,901; 3,589,903; 3,619,237; 3,653,907 and 3,664,842;

It has proved to be of advantage to use silver compounds which are essentially non-lightsensitive under the conditions of the process, for example the silver salts of aliphatic carboxylic acids with a thioether group described in U.S. Pat. No. 3,330,663 or silver salts of long-chain fatty acids such as silver behenate, silver palmitate, silver stearate, silver oleate, silver laurate, silver hydroxystearate, silver caprate and silver myristate.

Other typical silver salts suitable for use as oxidizing agents include, for example, silver benzoate, silver phthalazinone, silver benzotriazole, silver saccharin, silver-4'-n-octadecyloxy diphenyl-4-carboxylic acid, silver-o-amino-benzoate, silver acetamidobenzoate, silver furoate, silver camphorate, silver-p-phenylbenzoate, silver phenylacetate, silver salicylate, silver butyrate, silver terephthalate, silver phthalate, silver acetate and silver hydrogenphthalate.

The toner compounds used according to the invention can be used in combination with conventional organic reducing agents containing active hydrogen attached through O, N or C, for example with o-alkyl- or cycloalkyl-substituted phenols, di- and tri-hydroxy aryl-, aminophenol-, aminonaphthol-, p-phenylene diamine- and hydroxylamine derivatives, gallates, alkoxynaphthols, acetoacetonitriles, pyrazolidin-3-one and pyrazolin-5-one, indane dione-1,3-derivatives, hydroxytetronic acids, hydroxy tetronimides, reductones, for example anhydrodihydro pyrrolidinohexose reductone, ascorbic acid and hydroxychromane or hydroxycoumarane derivatives, for example according to Belgian Pat. No. 768,374 or U.S. Pat. Application Ser. No. 156,047 now U.S. Pat. No. 3,819,382. It is preferred to use, for example, o-alkyl-substituted phenols, hydroquinone, aminophenol and methoxynaphthol derivatives, bis-$\beta$-naphthols, hydroxycoumaranes and hydroxychromanes. The reducing agents can be used in the usual concentrations of from 0.1 to 2 mols and preferably in concentration of from 0.3 to 1.5 mols of reducing agent per mol of oxidizing agent, i.e. per mol of the non-light-sensitive organic silver salt. If added to an image-receiving layer, the reducing agents, preferably o-alkyl-substituted phenols, are preferably used in concentrations of from 0.3 to 0.7 mols. The same concentrations of reducing agents are applied in heat-sensitive layers.

Even in the modified form of the material according to the invention, in which light-sensitive heavy metal salts, especially silver salts, are present as light-sensitive compounds, the layers can be optically sensitized by the addition of dyes. Preferred sensitizers are compounds of the kind which are also normally used for optically sensitizing conventional silver halide emulsion layers, i.e. cyanine dyes, merocyanines, oxonols or isothiocyanines of a variety of different types, as described, for example, in F.M. HAMER's book entitled "The Cyanine Dyes and Related Compounds" (1964) published by Interscience Publishers a division of John Wiley & Sons, New York.

To prepare the material according to the invention, the components for the redox reaction and the light-sensitive heavy metal are used together with a suitable binder. Suitable binders include the usual natural or synthetic film-forming polymers, for example proteins, especially gelatin, alginic acid and derivatives thereof, starch ether or gallactomannan; preferred binders are organic polymers such as copolymers of vinyl chloride and vinyl acetate or copolymers of butadiene und styrene, polyethylene, polyamides, polyisobutylene, polyvinyl chloride, polyvinyl alcohol, polyvinyl acetate or completely or partially hydrolyzed polyvinyl acetate, polyvinylidene chloride, polyvinylpyrrolidone, polystyrene, chlorinated rubber, polyvinyl butyral, polymers of acrylic acid or methacrylic acid esters, acrylamide or copolymers of derivatives of acrylic acid and methacrylic acid, cellulose derivatives, especially cellulose ethers, cellulose esters such as carboxymethyl cellulose, nitrocellulose, cellulose acetate, cellulose propionates, or mixtures thereof, such as cellulose acetobutyrates.

The light-sensitive silver-salt-containing layer can be used as a self-supporting layer, although it is preferably applied to a suitable support. The layer support must be stable at the processing temperature of 80° to 200°C. Examples of suitable supports include sheets or films of paper, cellulose acetates, polyethylene terephthalate, textile fabrics, metal foils or glass. Where paper supports are used, the papers may contain the usual auxiliary layers, such as baryta coatings and polyethylene layers.

Inorganic or organic salts of silver, mercury or gold are examples of the light-sensitive heavy metal salts which are suitable for use in the first kind of processes and which on exposure to light form metal nuclei which are able to initiate the image-producing redox reaction. It is preferred to use heavy metals of Group Ib of the Periodic Table of Elements, especially silver salts and, among these, preferably silver halides.

The light-sensitive heavy metal salt particularly suitable for the particular redox system can be determined by a few small-scale tests. Thus, it is possible for example to mix the metal salt, in the form of an aqueous suspension, with the components of the redox reaction. The resulting mixture should not undergo any change in the dark. If this mixture is exposed to ultraviolet light, it should discolor relatively quickly. If these conditions apply, the heavy metal salt is suitable for the redox system.

The light-sensitive heavy metal salt is preferably used in relatively small quantities of from 0.1 to 10 % by weight, more preferably 0.2 to 1 % by weight, based on the weight of the oxidizing agent. This proportion of light-sensitive salt is sufficient for most systems. In exceptional cases, the proportion of light-sensitive salt can of course be outside the above range.

The light-sensitive heavy metal salt, for example the silver halide, is intended to be present in such small quantities that the photolytically formed heavy metal nuclei are able to initiate the redox reaction. However, the concentration of the silver halide should be so low that the copying material undergoes very little or no discoloration under the effect of the metal nuclei formed.

The silver halide can be added to the casting solution for the layer containing the components for the redox reaction, or can be prepared in situ in the casting solution, for example by precipitating the silver halide in the mixture. The silver ions for the precipitated silver halide can emanate essentially from the non-lightsensitive silver salt.

The silver halides can be prepared from the light-sensitive silver salts in different ways. For example, the surface of the non-lightsensitive silver salts can be treated with vapours of hydrohalic acids, for example hydrochloric, hydrobromic or hydroiodic acid. The quantities of silver halide formed on the surface can be kept within the required limits both through the concentration of the hydrogen halide in the vapour phase and through the treatment time.

The non-lightsensitive silver salts of the organic acids can of course also be treated with a solution containing halogen ions such as chlorine, bromine or iodine ions. Suitable are solutions of hydrohalic acids or their salts, especially their ammonium and alkali metal salts.

The non-lightsensitive silver salts are reacted with the compounds yielding halogen ions preferably in the form of a suspension in a volatile, non-aqueous liquid. It is also possible, however, to react the dry salts, for example with hydrohalide vapours.

In addition to hydrohalic acids and their salts, for example the already mentioned alkai metal, ammonium, alkaline earth metal or other metal salts, for example zinc and mercury salts, it is also possible to use ionizable organic halogen compounds, for example triphenylmethylchloride, triphenylmethyl-bromide, 2-bromo-2-methylpropane, 2-bromobutyric acid, 2-bromoethanol or benzophenone dichloride.

It is preferred to form the light-sensitive silver halides from the non-lightsensitive silver salts of the organic acids for preparing the materials according to the invention. This promotes the ability of the silver halides to form upon exposure photolytic silver nuclei which are particularly effective for initiating the redox reaction. Although separate preparation of the silver halides and their subsequent admixture with the non-lightsensitive silver salts also gives useful materials, the photolytic heavy metal nuclei formed from mixtures such as these are generally not as effective.

Some of the basically non-lightsensitive silver salts which can be used for the photographic material of the invention show a certain degree of natural sensitivity when precipitated in the presence of a protective colloid, for example a protein, especially gelatin, which is a technique normally adopted in the production of conventional silver halide emulsions. Accordingly, when precipitating the silver salts in the preparation of the material according to the invention, steps must be taken to ensure that the silver salts formed are non-lightsensitive. This is generally achieved by carrying out the precipitation in the absence of a protective colloid. This is true, for example, for the silver salts described in U.S. Pat. No. 3,330,663.

The dried silver salts are then added to the solutions or dispersions of the binding agent for the layer. The concentration of the silver salt in the binder dispersions may vary within wide limits, depending upon the required silver coverage in the photographic layers. In general, it is sufficient to use quantities of from 0.01 to 0.1 mol of silver salt per kilogram of casting solution. However, it is preferred to use from 0.02 to 0.05 mol of silver salt per kilogram of the solution or dispersion. The same also applies regarding the silver coverage of the finished photographic layer. In this case, too, the concentration can be varied within wide limits, depending upon both the required effect and upon the desired purpose. In general, the concentration of silver in the form of a silver salt, amounts to between 0.1 and 1.5 $g/m^2$ and preferably to between 0.2 and 1 $g/m^2$. It is of course also possible to use mixtures of different non-lightsensitive silver compounds in the material according to the invention.

To improve the photographic properties other non-lightsensitive heavy metal compounds can be added to the material, preferably to the layer containing the non-lightsensitive silver salt. It is possible in this way to obtain, for example, a reduction in fogging, an increase in density or a change in the color of the image, for example to neutral black.

Examples of heavy metal compounds of this kind include salts or compounds of mercury, cadmium, lead, uranium, gold, platinum, palladium or rhodium. The heavy metal compounds may actually be added during the precipitation of the silver salt. It is preferred to add solutions of the heavy metal salts and of the silver salts to the precipitation component introduced beforehand by the double-jet technique and, at the same time, to precipitate them. Although, simultaneous precipitation of the silver salt and of the heavy metal salt is of particular advantage and produces particularly favourable effects, depending upon the type of heavy metal salt used, the heavy metal salts can also be added in solid or dissolved form to the casting solutions already containing silver salt for the photographic layer. The heavy metal salts can also be mixed with the dried silver salts by grinding or added just before casting of the casting solution for the photographic layer. It is of course also possible to use combinations or different heavy metal salts.

The quantity in which the heavy metal salts or heavy metal compounds are added can vary within wide limits. Once again, the concentration is governed both by the type of heavy metal salt and silver salt and by the required effect. The optimum quantity can readily be determined by any person having ordinary skill in the art through a few small-scale tests. As a rule, concentrations of from 0.001 to 10 mol % and, preferably, from 0.01 to 5 mol %, are sufficient for obtaining the required effect. If the heavy metal salts are added at a later stage in the production of the photographic material before casting, it is sufficient to use concentrations of from 0.001 to 0.2 preferably from 0.005 to 0.7 mol of heavy metal salt, for example mercury(II) acetate, per mol of silver salt.

In addition, the image color and image density of the image-receiving material can be improved by adding certain metal salts, for example lead(II) stearate. Metal ion of this kind and their application are described in U.S. Pat. No. 3,460,946.

The layers can also contain white pigments, such as zinc oxide, silicon dioxide or titanium dioxide, as fillers for improving the white areas, and terpene resins and organic acids for influencing the tendency of the layers to stick and for improving their stability in storage. Layers of this kind are described in U.S. Pat. Nos. 3,074,809 and 3,107,174.

One factor governing selection of the binders for the light-sensitive layer and the image-receiving layer is that the layers should adhere to one another on heating. However, these difficulties are known from other conventional processes, for example the silver salt diffusion or heat development processes, and can readily be solved on the basis of experience gained in these known fields.

The light sources normally used for reproduction purposes, such as halogen, iodine-quartz or incandescent electric lamps, can be used for exposing the light-sensitive layers. The choice of the light source to be used depends on the spectral sensitivity of the heavy metal salt or sensitizing dye used. The exposure time amounts to a few seconds.

The silver-salt-containing light-sensitive copying materials are developed under heat at temperatures of from 80° to 200°C. Heatable presses, drying drums, rollers or the apparatus described in U.S. Pat. No. 3,249,738 or French Pat. Nos. 1,419,101; 1,416,752 and 1,512,332, and standard apparatus can be used for developing the copying materials.

To protect the layer and to produce a high-gloss image the light-sensitive layer can be developed under heat in contact with a smooth film, for example a polyester film. The most favourable temperature and heating time depend, of course, on the composition of the light-sensitive photographic material. The development time amounts to between 3 and 80 seconds, depending both upon the temperature level (80° to 200°C) and the apparatus used.

The image-producing compounds are transferred from the unexposed areas of the light-sensitive layers to the image-receiving layer at an elevated temperature of from 80° to 200°C. Heating can be carried out, for example by guiding the exposed light-sensitive layer in contact with the image-receiving layer over hot plates or rollers or even by irradiation with IR-light. The most favourable temperature and heating time depend on the type of image-producint compound and on the composition of the non-lightsensitive silver-salt-containing copying material; they can readily be determined by a few simple test.

The thermosensitive recording material of the third embodiment of the present invention is not photosensitive and contains in the presence of said toning agent of the quinazoline dione, benzoxazine dione or napthoxazine dione series, a non-photosensitive reducible silver salt that at least at the moment of heating said materials can come into reactive contact with a reducing agent as described above.

The non-photosensitive silver salt and reducing agent may be present in the same binder layer or in adjacent layers from which one compound, e.g. the reducing agent are transferred upon heating into the adjacent layer containing the reducible silver salt.

Heat-sensitive recording materials of the present invention may be used in any process in which heat is applied information-wise to or generated in the recording material, e.g. by means of hot bodies, for example a hot stylus or by means of heat-producing radiation, e.g. infrared radiation.

Heat sensitive sheet-like recording materials of the present invention are particularly suited for the thermographic copying of originals containing infrared-absorbing image markings. When the original in contact with the present recording materials is exposed to infrared radiation, the infrared-absorbing image portions of the original are heated selectively and by heat transfer cause the formation in the contacting heat-sensitive sheet of a visible color change resulting from the reaction of the organic reducing agent with the reducible reaction partner, i.e. the non-light-sensitive silver salt.

EXAMPLE 1

Light-sensitive material:

An equimolar mixture of silver behenate and behenic acid is prepared by precipitating silver nitrate with a solution of sodium behenate and behenic acid in alcohol and water. The precipitate is carefully washed and dried.

The suspension for preparing the layer is prepared by stirring the following mixture with a magnetic stirrer for 6 hours in the presence of glass beads:

1.8 g of silver behenate-behenic acid (molar ratio 1:1);

a toner in the quantity specified in the following Table;

5 mg of 1,1-bis-(benzotriazolyl)-mercury(II);

1.5 g of cellulose acetobutyrate;

0.75 g of a copolymer of vinyl chloride and vinyl acetate (ratio by weight 60:40);

40 g of butanone.

0.5 g of the sensitizer 5-[(3-ethylthiazolidin-2-ylidine)ethylidene]-3-allyl-2-thiooxazolidine-2,4-dione, dissolved in 0.5 ml of butanone, and 1 g of bis- (2-hydroxy-3-tert.butyl-5-methylphenyl)-methane, are added with stirring to this suspension before casting.

The casting solution is applied to a layer support of paper and dried. The silver coverage amounts to between 0.6 and 0.8 g/m$^2$ of silver in the form of the silver compound.

The mixture described above is prepared several times. To each separate preparation there is added before stirring, a toner compound. The toners specified in the following Table are added to the individual samples in the quantities specified.

The photographic material thus produced is exposed in a conventional copying device equipped with an incandescent tungsten lamp for 30 seconds through a $\sqrt{2}$ - test wedge and then developed by heating to a temperature as shown in the following Table 1. Brown to black images of the test wedge are obtained. The maximum density and the uniform fog of the exposed respectively unexposed samples (the unexposed samples were developed under identical conditions) were measured to common practice with a densitometer. In order to protect the layer development was performed with a polyester foil being in contact with the layer-side of the material.

The excellent effect of the toner compounds of the present invention is shown by comparison with the control sample containing no toner which yields only yellow images of poor density.

The improved stability of the materials according to the invention is evident from comparison with the last two samples of the following Table which contain the known toner phthalimide or phthalazinone. The material of the present invention can be processed at higher temperatures, with longer heating time and in higher concentration and still have similar or even lower undesired uniform fog as compared with the comparison samples. The sensitivity and the maximum density is in most cases higher.

Table 1

| Compound No. | g/mixture | Developing Temperature °C | Developing Time sec. | Sensitivity stages $\sqrt{2}$ | Maximum density | Fog | Image color |
|---|---|---|---|---|---|---|---|
| Control sample | | 127 | 40 | — | 0.17 | 0.15 | yellow |
| 1 | 1.8 | 93 | 60 | 24 | 1.23 | 0.23 | olive-black |
| 3 | 4.2 | 104 | 10 | 23 | 1.15 | 0.17 | brown-black |
| 6 | 0.3 | 93 | 10 | 22 | 1.41 | 0.23 | black |
| 7 | 2.7 | 137 | 80 | 23 | 0.94 | 0.18 | dark grey |
| 9 | 2.4 | 116 | 10 | 24 | 1.35 | 0.23 | black |
| 10 | 0.65 | 93 | 15 | 23 | 1.36 | 0.18 | black |
| 10 | 2.6 | 93 | 15 | 23 | 1.27 | 0.23 | black |
| 11 | 0.7 | 93 | 20 | 24 | 1.39 | 0.21 | black |
| 12 | 0.66 | 116 | 7.5 | 22 | 1.37 | 0.16 | black |
| 12 | 1.31 | 116 | 7.5 | 25 | 1.30 | 0.21 | black |
| 13 | 0.66 | 104 | 10 | 23 | 1.26 | 0.20 | brown-black |
| 14 | 1.6 | 116 | 10 | 20 | 1.27 | 0.25 | black |
| 15 | 1.5 | 116 | 10 | 21 | 1.27 | 0.25 | black |
| 16 | 0.7 | 104 | 15 | 21 | 1.21 | 0.18 | black |
| 17 | 1.4 | 122 | 7.5 | 23 | 1.16 | 0.24 | olive-black |
| 20 | 1.5 | 126 | 10 | 20 | 1.18 | 0.15 | brown |
| 25 | 1.1 | 93 | 5 | 21 | 1.20 | 0.23 | black |
| 26 | 1.1 | 116 | 10 | 18 | 1.24 | 0.21 | black |
| 27 | 0.73 | 93 | 10 | 22 | 1.29 | 0.24 | black |
| 27 | 1.46 | 93 | 10 | 22 | 1.27 | 0.23 | black |
| 28 | 0.66 | 93 | 15 | 22 | 1.31 | 0.25 | black |
| 28 | 2.62 | 93 | 15 | 22 | 1.24 | 0.24 | black |
| 29 | 0.60 | 93 | 10 | 21 | 1.22 | 0.21 | black |
| 29 | 2.42 | 93 | 15 | 21 | 1.38 | 0.19 | black |
| 30 | 0.66 | 104 | 7.5 | 23 | 1.26 | 0.20 | black |
| 30 | 2.62 | 104 | 7.5 | 23 | 1.22 | 0.18 | black |
| 32 | 1.32 | 104 | 7.5 | 23 | 1.24 | 0.20 | black |
| 32 | 2.64 | 104 | 10 | 23 | 1.22 | 0.23 | black |
| 34 | 0.66 | 93 | 10 | 18 | 1.12 | 0.24 | brown-black |
| 35 | 1.4 | 116 | 20 | 20 | 1.11 | 0.18 | black |
| 36 | 0.66 | 104 | 30 | 24 | 1.31 | 0.23 | black |
| 36 | 2.2 | 93 | 80 | 23 | 1.21 | 0.19 | black |
| phthalimide | 0.6 | 88 | 15 | 23 | 0.92 | 0.26 | brown |
| phthalazinone | 1 | 88 | 10 | 21 | 1.20 | 0.23 | black |

EXAMPLE 2

The following layers are applied to a layer support of baryta-coated paper:

1. A light-sensitive layer from the following casting solution
   - 1.8 g of silver behenate-behenic acid (molar ratio 1:1);
   - 3.0 g of cellulose acetate;
   - 4.5 ml of a 1 % by weight calcium bromide solution in methanol;
   - 5.7 ml of a 1 % by weight solution in methanol of mercury(II) acetate acidified by the addition of glacial acetic acid;
   - 3.0 ml of a 0.01 % solution of 1-methyl-3-allyl-5-[2-(3-ethylbenzoxazol-2-ylidene)-ethylidene]-2-thiohydantoin in chloroform;
   - 0.15 g of silicon dioxide;
   - 55.0 g of acetone;
   - 1.0 g of a copolymer of vinyl chloride and vinyl acetate (ratio by weight 88:12) dissolved in
   - 25 g of butanone and a toner in the quantity specified in the following Table.
2. Covering layer from the following casting solution:
   - 10 g of polyvinyl butyral;
   - 100 g of acetone and
   - a toner and a developer in the respective quantities specified in the following Table.

Before application, the casting solution for the light-sensitive layer is ground for 16 hours in a ball mill.

The light-sensitive layer contains 0.6 – 0.8 g/m$^2$ of silver in the form of the silver salts indicated.

The covering layer is applied to the dried light-sensitive layer. The concentration of the reducing agent in the covering layer amounts to between 0.5 and 1.5 g/m$^2$.

The light-sensitive material is exposed through a transparent original to the light of tungsten lamps for a period of 3 to 30 seconds, depending both upon their intensity and upon the required gradation, and developed by heating.

To protect the layer and to obtain a high-gloss image, the layer side of the material can be developed under heat in contact with a polyester film.

Brown, brown-black, olive-black, grey to neutral-black images on a white to yellow background are obtained after development, depending both upon the type of developer and toner combination used and upon the processing conditions.

5 mg of 1,1'-bis-(benzotriazolyl)-mercury(II);

1.5 g of cellulose acetobutyrate;

0.75 g of a copolymer of vinyl chloride and vinyl acetate (ratio by weight 60:40);

40 g of butanone;

0.5 mg of the sensitizer 5-[(3-ethylthiazolidin-2-ylidene)-ethylidene]-3-allyl-2-thiooxazolidin-2,4-dione, dissolved in 0.5 ml of butanone, and a developer and toner compound in the quantity specified in the following Table, are added with stirring to this suspension before casting.

The casting solution is applied to a paper support and dried. The silver coverage amounts to between 0.6 and 0.8 g/m$^2$ of silver in the form of the silver compound.

The light-sensitive material is exposed through a transparent original to the light of a tungsten lamp for a period of 3 to 30 seconds, according both to their intensity and to the required gradation, and developed by heating.

Table 2

| Compound No. | Light-sensitive layer / g | Cover layer g | Developer | g | Image color |
|---|---|---|---|---|---|
| Control sample | | — | bis-(2-hydroxy-3-tert.-butyl-5-methylphenyl)-methane | 8 | yellow-orange |
| 12 | 1.0 | 1 | bis-(2-hydroxy-3-tert.-butyl-5-methylphenyl)-methane | 8 | olive-black |
| 30 | 2.0 | 1 | bis-(2-hydroxy-3-tert.-butyl-5-methylphenyl)-methane | 8 | olive-black |
| 12 | 1.5 | 1 | 1-(p-aminophenyl)-3,4-dimethyl-pyrazolin-5-one | 5 | dark brown |
| 36 | 2.0 | 1 | 2,2'-dihydroxy-1,1'-binaphthyl | 8 | olive-black |
| 36 | 2.0 | 1 | bis-(2-hydroxy-1-naphthyl)-methane | 8 | black |
| 36 | 2.0 | 1 | 1,1,5,5-tetra-(2-hydroxy-3,5-dimethylphenyl)-2,4-ethyl-pentane | 8 | black |

EXAMPLE 3

Light-sensitive material:

Silver behenate is prepared by precipitating aqueous ammonium behenate solution with ammoniacal silver nitrate solution at 90°C, followed by acidification with nitric acid. The precipitate is carefully washed and dried.

The suspension for preparing the layer is prepared by stirring the following mixture for 6 hours with a magnetic stirrer in the presence of glass beads:

1.03 g of silver behenate;

0.6 g of behenic acid;

a toner in the quantity specified in the following Table;

To protect the layer and to produce a high-gloss image, the layer side of the material can be developed by heating in contact with a polyester film.

Brown, brown-black to neutral-black images on a white to yellow background are obtained after development, depending both upon the type of developer and toner combination used and upon the processing conditions.

Instead of adding 1,1'-bis-(benzotriazolyl)-mercury(II) it is also possible to add 50 mg of mercury(II) acetate, 100 mg of N,N'-bis-(succinimide)-mercury(II) or 50 mg of bis-(2H-1-oxophthalazin-2-yl)-mercury(II).

Table 3

| Compound No. | g | Developer | g | Maximum density | Fog | Color |
|---|---|---|---|---|---|---|
| 6 | 0.6 | 2-octylhydroquinone | 1.2 | 1.21 | 0.24 | black |
| 6 | 0.6 | (2,5-dihydroxyphenyl)-(1-phenyl-tetrazol-5-yl)-sulfide | 1.8 | 1.18 | 0.21 | black |
| 10 | 0.65 | 1,1-bis-(2-hydroxy-3,5-dimethyl-phenyl)-2-methylpropane | 3.4 | 1.02 | 0.22 | brown-black |
| 12 | 0.66 | 2,2'-dihydroxy-1,1'-binaphthyl | 1.7 | 1.03 | 0.16 | black |
| 13 | 0.66 | 2,2-dimethyl-6-hydroxy-chromane | 1.0 | 0.89 | 0.18 | brown |
| 15 | 1.5 | 2-ethoxy-3,3-dimethyl-5-hydroxy-coumarane | 1.5 | 0.86 | 0.18 | brown |
| 25 | 1.1 | 2,3-dihydroxy-naphthalene | 1 | 1.08 | 0.25 | black |
| 26 | 1.1 | pyrocatechol | 0.7 | 0.92 | 0.25 | black |
| 27 | 1.46 | 2-methoxy-3,3-dimethyl-5-hydroxy-coumarane | 1.2 | 1.12 | 0.15 | black |
| 30 | 2.62 | 4-hydroxyphenyl-carbamic acid ethylester | 1.1 | 0.96 | 0.19 | black |
| 36 | 0.66 | 2,5-di-tert.-butyl-hydroquinone | 3.0 | 1.29 | 0.16 | black |

EXAMPLE 4

Image-receiving material:

An image-receiving layer is prepared from the following casting solution:

1.05 g of silver behenate and behenic acid (molar ratio 1:1);

a toner in the quantity specified in the following Table;

0.83 g of terpene resin;

2.4 g of zinc oxide;

0.28 g of silicon dioxide;

0.185 g of 2,6-di-tert.-butyl-p-cresol;

7.5 g of an 8 % ethylmethacrylate solution in 3-pentanone;

40 g of a 1.5 % polyvinyl acetate solution in butylacetate;

7.5 g of butylacetate.

The mixture are ground for 16 hours in a ball mill, subsequently applied to a paper support and dried. The dried layer contains 0.3 to 0.4 g/m$^2$ of silver in the form of silver behenate.

Light-sensitive material:

A light-sensitive material is prepared by applying a casting solution of the following composition to a semi-transparent paper support followed by drying at room temperature:

6.0 mg of erythrosine;

125.0 mg of 4-methoxy-1-naphthol;

1.5 g of ethylcellulose;

70 ml of ethylacetate;

5 ml of methanol.

The light-sensitive layer is imagewise exposed and heated for 10 seconds to 130°C in a conventional heat development apparatus in contact with the above image-receiving layer. The samples were processed fresh and after storage for 48 hours at 50°C in a heating cabinet. The maximum density and uniform fog are measured with a densitometer. Brown to black or blue-black images of high density are obtained.

When an image-receiving material is prepared without toners, but with otherwise the same composition, yellow to yellowish-olive images of insufficient density are obtained.

The improved stability of the materials according to the invention is shown by comparison with conventional toners, for example phthalazinone. In the majority of toners according to the invention, density is decreased to a lesser extent and the fog increased to a lesser extent than with phthalazinone in consequence of storage in the heating cabinet.

Table 4

| Compound No. | g | Fresh Test | | Heating-cabinet Test | | Image color |
|---|---|---|---|---|---|---|
| | | Maximum density | Fog density | Maximum | Fog | |
| Control sample | | 0.59 | 0.05 | 0.35 | 0.07 | yellow-olive |
| 1 | 0.50 | 0.94 | 0.05 | 0.93 | 0.07 | brown |
| 3 | 1.05 | 0.85 | 0.06 | 0.83 | 0.08 | brown |
| 6 | 0.26 | 1.13 | 0.05 | 1.09 | 0.06 | black |
| 7 | 0.15 | 0.88 | 0.06 | 0.86 | 0.08 | brown |
| 9 | 0.52 | 1.02 | 0.06 | 1.04 | 0.07 | black |
| 10 | 0.12 | 1.00 | 0.04 | 0.95 | 0.04 | blue-black |
| 11 | 0.15 | 0.88 | 0.06 | 0.89 | 0.06 | brown |
| 12 | 0.28 | 0.92 | 0.05 | 0.92 | 0.05 | brown-black |
| 13 | 0.14 | 1.09 | 0.04 | 1.10 | 0.06 | brown-black |
| 14 | 0.69 | 1.06 | 0.04 | 1.04 | 0.05 | black |
| 15 | 0.65 | 0.97 | 0.05 | 0.95 | 0.06 | brown-black |
| 16 | 0.61 | 1.00 | 0.04 | 1.02 | 0.05 | black |
| 17 | 0.60 | 0.83 | 0.07 | 0.79 | 0.08 | olive-brown |
| 20 | 0.16 | 0.81 | 0.05 | 0.80 | 0.05 | brown |
| 25 | 0.48 | 0.97 | 0.04 | 0.99 | 0.05 | blue-black |
| 26 | 0.12 | 0.86 | 0.05 | 0.83 | 0.06 | brown |
| 27 | 1.26 | 1.04 | 0.05 | 1.04 | 0.06 | blue-black |
| 28 | 0.32 | 1.12 | 0.05 | 1.15 | 0.06 | black |
| 29 | 1.06 | 1.10 | 0.06 | 1.01 | 0.07 | black |
| 30 | 1.12 | 0.94 | 0.05 | 0.90 | 0.06 | brown-black |
| 32 | 0.28 | 1.12 | 0.05 | 1.10 | 0.06 | black |
| 34 | 1.12 | 1.06 | 0.05 | 1.05 | 0.06 | black |
| 35 | 0.60 | 0.78 | 0.04 | 0.75 | 0.05 | olive-brown |
| 36 | 1.12 | 0.97 | 0.05 | 0.97 | 0.06 | brown-black |
| 37 | 0.17 | 0.79 | 0.04 | 0.75 | 0.05 | brown |
| phthalazinone | 0.43 | 0.98 | 0.05 | 0.78 | 0.08 | black |

EXAMPLE 5

Image-receiving material:

An image-receiving layer is prepared from the following casting solution:

1.5 g of silver stearate;

0.3 g of stearic acid;

1.6 g of a copolymer of n-butylmethacrylate and isobutylmethacrylate (ratio by weight 50:50);

a toner in the quantity specified in the following Table;

6.88 g of zinc oxide;

80 g of ethylacetate.

The mixture is ground for 16 hours in a ball mill and, following the addition of 0.5 g of 2,6-dicyclohexyl-4-methylphenol dissolved in 25 g of ethylacetate, is applied to a paper support and dried. The dried layer contains from 0.5 to 0.6 g/m$^2$ of silver in the form of silver stearate.

Light-sensitive material:

The light-sensitive material is prepared by applying a casting solution of the following composition to a semi-transparent paper support followed by drying at room temperature:

6.0 mg of 1,4-diethyl-2-thio-5-[4-carboxymethoxycinnamylidene]-barbituric acid;

125.0 mg of 2-(p-chlorophenol)-acetoacetonitrile;

30.0 mg of o-tolylbiguanide;

2.5 g of ethylcellulose;

70.0 ml of ethylacetate;

5.0 ml of methanol.

The light-sensitive layer is imagewise exposed and thereafter in contact with the image-receiving layer described above in the same way as described in Example 4. Dark-brown to black images of high density are obtained with the toners identified in the following Table.

Instead of adding 2,6-dicyclohexyl-4-methylphenol, it is also possible to add 0.37 g of 2,6-di-tert.butyl-4-hydroxymethylphenol.

The better stability of the materials according to the invention is shown by comparison with a conventional toner, for example phthalazinone. In the majority of toners according to the invention, density is decreased to a lesser extent and undesired fog increased to a lesser extent than with phthalazinone in consequence of storage in a heating cabinet. In addition, the fog of fresh samples is lower in the case of the toners according to the invention than in the case of phthalazinone.

Table 5

| Compound No. | g | Fresh Test: Maximum density | Fresh Test: Fog | Heating-cabinet Test: Maximum density | Heating-cabinet Test: Fog | Image color |
|---|---|---|---|---|---|---|
| Control sample | | 0.39 | 0.04 | 0.39 | 0.08 | orange |
| 6 | 0.92 | 0.91 | 0.07 | 0.87 | 0.08 | brown-black |
| 10 | 0.25 | 0.95 | 0.06 | 0.94 | 0.08 | brown-black |
| 14 | 0.92 | 0.95 | 0.07 | 0.74 | 0.09 | brown-black |
| 16 | 1.08 | 0.91 | 0.07 | 0.86 | 0.10 | brown-black |
| 25 | 0.82 | 0.95 | 0.06 | 0.91 | 0.10 | brown-black |
| 27 | 1.10 | 0.90 | 0.07 | 0.90 | 0.10 | dark brown |
| 34 | 1.12 | 0.91 | 0.06 | 0.94 | 0.11 | brown-black |
| phthalazinone | 0.38 | 0.98 | 0.09 | 0.51 | 0.12 | brown-black |

EXAMPLE 6

An image-receiving layer is prepared from the following casting solution:

0.68 g of silver-2-(tetradecylthio)-5-(carboxylatomethylthio)-1,3,4-thiadiazole;
0.28 g of compound 28;
0.83 g of terpene resin;
0.3 g of behenic acid;
2.4 g of zinc oxide;
0.28 g of silicone dioxide;
0.185 g of 2,6-di-tert.-butyl-p-cresol;
7.5 g of an 8 % ethylmethacrylate solution in butylacetate;
40.0 g of a 1.5 % polyvinyl acetate solution in butylacetate;
7.5 g of butylacetate.

The mixture is ground for 16 hours in a ball mill, subsequently applied to a paper support and dried. The dried layer contains 0.3 to 0.4 g/m² of silver in the form of the silver salt.

The light-sensitive layer described in Example 4 is imagewise exposed and heat-developed in contact with the above image-receiving layer in the same way as described in that Example. A dark-brown image with a density of 0.81 is obtained.

Instead of using the aforementioned silver salt, it is also possible to use 0.62 g of silver octadecylthioglycolate.

EXAMPLE 7

The following mixture is ground in a ball mill for 12 hours:

40.0 g of ethyl acetate;
7.0 g of stearic acid;
0.6 g of polymethylacrylate (viscosity of a 5 % by weight solution in chloroform at 20°C is 0.91 cP);
0.6 g of cellulose acetobutyrate (substitution acetat and butyrate is 0.5 and 2.4 respectively; the viscosity of 20 % by weight solution in aceton is 15 cP);
0.25 g of toner compound 6;
4.1 g of zinc oxide (average grain size 10/μm),
0.9 g of silver stearate.

Before casting the following ingredients are added 20.0 g of ethyl acetate;

0.3 g of 3,4,5-Trihydroxybenzoic acid ethylester.

The mixture thus obtained is applied onto a support of polyethyleneterephthalate. The dried layer contains 0,65 g in the form of the silver salt/m².

The dried layer is exposed in a heat copying device in contact with the original to be reproduced. The original is a printed paper carrying an information which was printed on with a black pigment containing carbon black.

The copying device used is the Thermofax copying apparatus model 47-3M by Minnesota Mining and Manufacturing Co., St.Paul, Minn.

A deep black copy with high contrast of the original is obtained. A comparison test with a material which contain no toner yields a brownish copy with insufficient density.

We claim:

1. In a photographic radiation sensitive recording material having therein a radiation sensitive composition and at least one layer containing dispersed in a binding agent a substantially non-light sensitive silver salt, a reducing agent for the non-light sensitive silver salt, and a toner compound, the improvement which comprises the toner being a heterocyclic toner compound of the following formula:

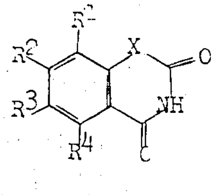

in which

X represents 0 or N-R⁵, $R^1$, $R^2$ $R^3$ or $R^4$represent hydrogen, alkyl, cycloalkyl, alkoxy, alkylthio, hydroxy, dialkylamino or halogen, in addition to which $R^1$ and $R^2$ or $R^2$ and $R^3$ or $R^3$ and $R^4$ can represent the ring members required to complete an anellated aromatic ring, and $R^5$ presents alkyl.

2. The photographic material of claim 1, wherein the non-light sensitive silver salt is a silver salt of a long-chain fatty acid.

3. The photographic material of claim 2, wherein the silver salt is a silver behenate or a silver stearate.

4. The photographic material of claim 2, wherein the said layer or an adjacent layer contains the heterocyclic toner in quantities of from 0.2 to 6 mol per mol of the non-light sensitive silver salt.

5. The photographic material of claim 2, wherein $R^1$, $R^2$, $R^3$ or $R^4$ represent hydrogen, methyl, methoxy, dimethylamino or diethylamino.

6. The photographic material of claim 2, which contains in addition a light-sensitive heavy metal compound and/or a polymethine sensitizer for sensitizing the non-light sensitive silver salt.

7. The photographic material of claim 6, which contains the light-sensitive heavy metal compound in the said layer in quantities of from 0.5 to 0.2% by weight, based on the weight of the non-light sensitive silver salt.

8. The photographic material of claim 6, which contains the polymethine sensitizer in quantities sufficient for sensitizing the non-light sensitive silver salt in the said layer and the reducing agent in the said layer or in a layer adjacent thereto.

9. The photographic material of claim 7, in which the light sensitive heavy metal compound is silver halide.

10. The photographic material of claim 6, which contains in addition a mercury(II)compound.

11. The photographic material of claim 1, which contains as reducing agent a compound containing at least one active hydrogen atom attached to oxygen, nitrogen or carbon.

12. The photographic material of claim 11, wherein the reducing agent is an o-alkyl- or cycloalkyl-substituted phenol, a 6-hydroxychromane, a 5-hydroxycoumarane, a di- or trihydroxyaryl derivative, an aminophenol, an aminonaphthol, a pyrazolin-5-one, a hydroxylamine derivative or an ascorbic acid derivative.

13. The photographic material of claim 11, wherein the reducing agent is a bis-$\beta$-naphthol or a bis-o-cycloalkyl or alkyl phenol.

* * * * *